(12) United States Patent
Buchanan et al.

(10) Patent No.: US 7,081,556 B2
(45) Date of Patent: ***Jul. 25, 2006

(54) AROMATICS CONVERSION WITH ITQ-13

(75) Inventors: John Scott Buchanan, Lambertyville, NJ (US); Jihad Mohammed Dakka, Whitehouse Station, NJ (US); Xiaobing Feng, Houston, TX (US); Jose Guadalupe Santiesteban, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 468 days.

This patent is subject to a terminal disclaimer.

(21) Appl. No.: 10/285,917

(22) Filed: Nov. 1, 2002

(65) Prior Publication Data

US 2004/0087822 A1    May 6, 2004

(51) Int. Cl.
*C07C 2/68*    (2006.01)
*C07C 5/22*    (2006.01)
*C07C 4/12*    (2006.01)

(52) U.S. Cl. ...................... 585/467; 585/475; 585/481; 585/489

(58) Field of Classification Search ................. 585/467, 585/475, 481, 489, 418, 430, 469; 208/135
See application file for complete search history.

(56) References Cited

U.S. PATENT DOCUMENTS

| 6,281,406 B1 | 8/2001 | Cain |
| 6,471,941 B1 | 10/2002 | Boix et al. |
| 6,709,572 B1 * | 3/2004 | Corma ........................ 208/113 |

FOREIGN PATENT DOCUMENTS

| WO | WO 98/51409 | 11/1998 |
| WO | WO 02/062734 | 8/2002 |
| WO | WO 03/076550 | 9/2003 |

OTHER PUBLICATIONS

U.S. Appl. No. 09/866,907, filed May 29, 2001, Girones et al.
U.S. Appl. No. 60/362,100, filed Mar. 5, 2002, Corma.
Armor, J.N., "New catalytic technology commercialized in the USA during the 1990s", Applied Catalysis A: General, Elsevier Science, Amsterdam, NL, vol. 222, No. 1-2, Dec. 20, 2001, pp. 407-426.

* cited by examiner

*Primary Examiner*—Thuan D Dang

(57) ABSTRACT

There is provided a process for aromatics conversion by contacting a feed suitable for aromatics conversion under conversion condition and in the presence of a catalyst comprising ITQ-13. Examples of such conversion processes include isomerization of aromatic (xylenes) feedstock, disproportionation of toluene to benzene and xylenes, alkylation and transalkylation of aromatics, conversion of light paraffins and light olefins to aromatics, conversion of naphtha to aromatics, and conversion of alcohol to aromatics.

34 Claims, 6 Drawing Sheets

AROMATICS CONVERSION WITH ITQ-13

BACKGROUND TO THE INVENTION

1. Field of the Invention

This invention relates to aromatics conversion in the presence of a catalyst comprising ITQ-13.

2. Description of the Prior Art

Many aromatic hydrocarbons are valuable commercial products. For example, para-xylene is a very valuable commercial product useful in the production of polyester fibers.

Aromatic compounds can be formed by converting non-aromatic compounds to aromatic compounds. An example of such a conversion is the dehydrocyclo-oligomerization of aliphatic hydrocarbons to form aromatics. This process typically uses an intermediate pore size zeolite catalyst such as ZSM-5. Another process for converting non-aromatic compounds to aromatic compounds involves reforming where $C_6$ and higher carbon number reactants, primarily paraffins and naphthenes, are converted to aromatic compounds. This process typically uses monofunctional large pore zeolites, such as zeolites L, Y, and X or bifunctional catalysts which can comprise a metal oxide support acidified by a halogen.

Also, less valuable aromatic compounds can be converted into more valuable aromatic compounds. Examples of such processes include the methylation of toluene to form xylenes, the disproportionation of toluene to form xylenes and benzene, and the isomerization of xylene feedstock to produce a product enriched in para-xylene. These processes typically use a catalyst comprising an intermediate pore size zeolite catalyst such as ZSM-5.

Co-pending U.S. patent application Ser. No. 09/866,907, filed May 29, 2001, describes a synthetic porous crystalline material, ITQ-13, which is a single crystalline phase material having a unique 3-dimensional channel system comprising three sets of channels, two defined by 10-membered rings of tetrahedrally coordinated atoms and the third by 9-membered rings of tetrahedrally coordinated atoms. Co-pending U.S. Patent Application Ser. No. 60/362,100, filed Mar. 5, 2002, describes a process for cracking hydrocarbons using a catalyst comprising ITQ-13.

SUMMARY OF THE INVENTION

The present invention is directed to a process for aromatics conversion by contacting a feed suitable for aromatic conversion under conversion conditions and in the presence of a catalyst comprising a synthetic porous crystalline material having a 3-dimensional channel system comprising a first set of generally parallel channels each of which is defined by a 10-membered ring of tetrahedrally coordinated atoms, a second set of generally parallel channels which are also defined by 10-membered rings of tetrahedrally coordinated atoms and which intersect with the channels of the first set, and a third set of generally parallel channels which intersect with the channels of said first and second sets and each of which is defined by a 9-membered ring of tetrahedrally coordinated atoms.

In a preferred embodiment, the present invention is directed to a process for converting feedstock comprising aromatic compounds to a product comprising aromatic compounds which differ from said feedstock. The process is carried out by contacting the feedstock containing the aromatic compounds under conversion conditions and in the presence of a catalyst composition comprising a synthetic porous crystalline material comprising a framework of tetrahedral atoms bridged by oxygen atoms, the tetrahedral atom framework being defined by a unit cell with atomic coordinates in nanometers shown in Table 1, wherein each coordinate position may vary within ±0.05 nanometer. Examples of such processes include the disproportionation of toluene to produce benzene and xylenes, ethylbenzene conversion, the isomerization of xylenes, and the alkylation of aromatic hydrocarbons.

In another preferred embodiment, the present invention is directed to a process for converting non-aromatic compounds to aromatic compounds. The process is carried out by contacting the non-aromatic compounds under conversion conditions and in the presence of a catalyst composition comprising a synthetic porous crystalline material comprising a framework of tetrahedral atoms bridged by oxygen atoms, the tetrahedral atom framework being defined by a unit cell with atomic coordinates in nanometers shown in Table 1, wherein each coordinate position may vary within ±0.05 nanometer. Examples of such processes include the catalytic reforming of naphtha and the dehydrocyclo-oligomerization of $C_2$–$C_5$ aliphatic hydrocarbons.

DETAILED DESCRIPTION OF THE PREFERRED EMBODIMENTS

Figure 1:
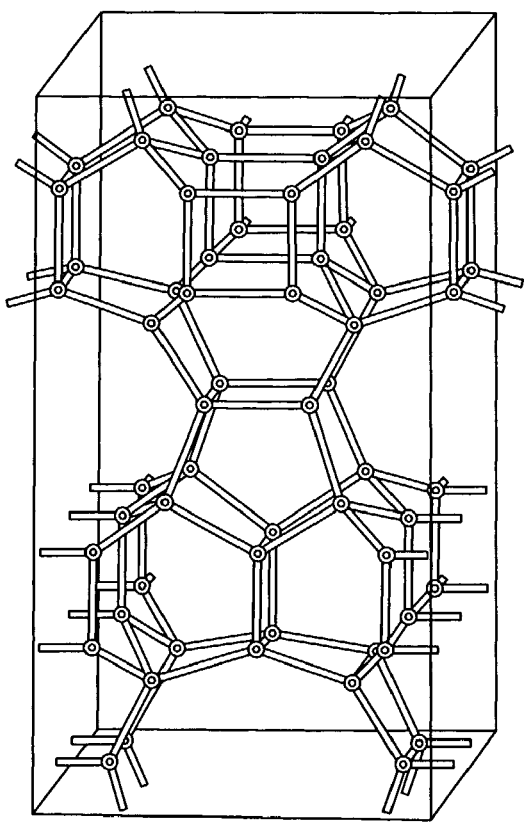
FIG. 1 is a schematic illustration of a unit cell of ITQ-13, showing the positions of the tetrahedral atoms.
Figure 2:
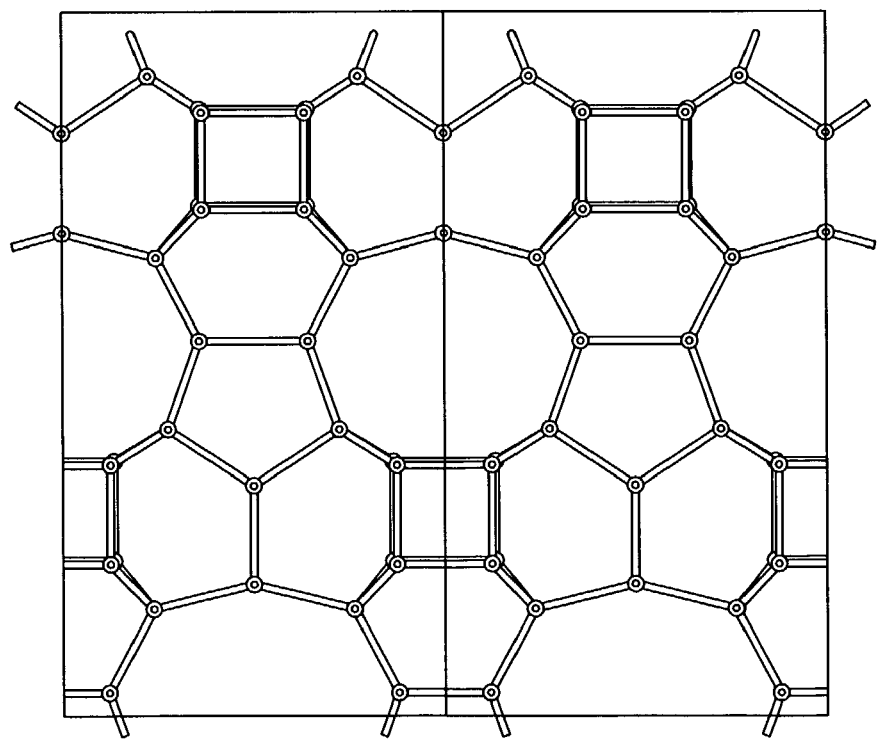
FIG. 2 is a schematic illustration of the nine-ring channel system of ITQ-13, again showing the positions of the tetrahedral atoms.
Figure 3:
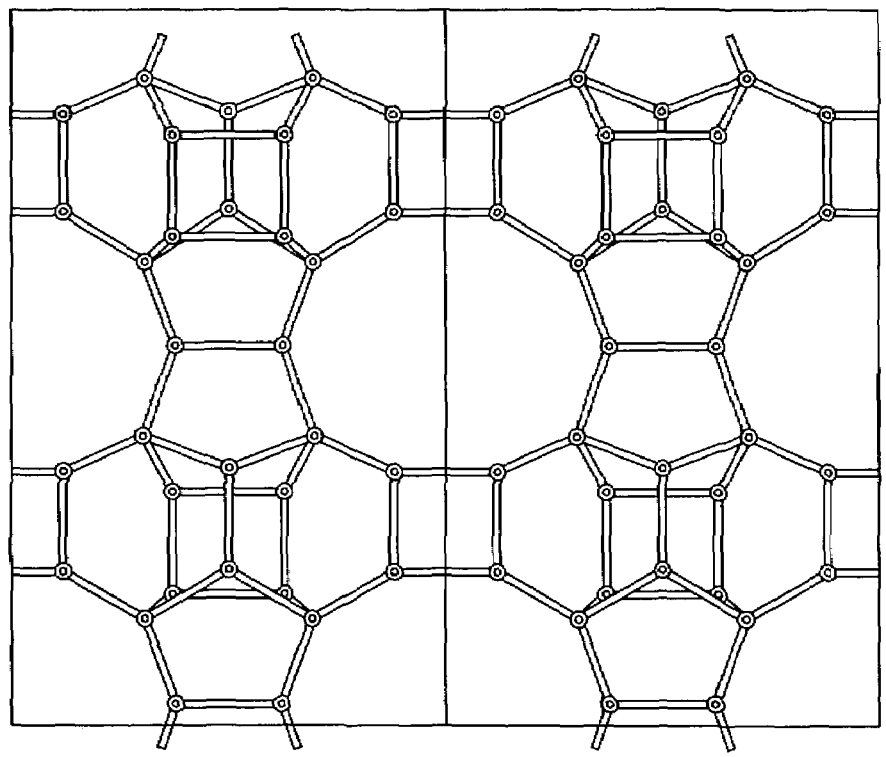
FIGS. 3 and 4 are illustrations similar to FIG. 2 of the ten-ring channel systems of ITQ-13.
Figure 4:
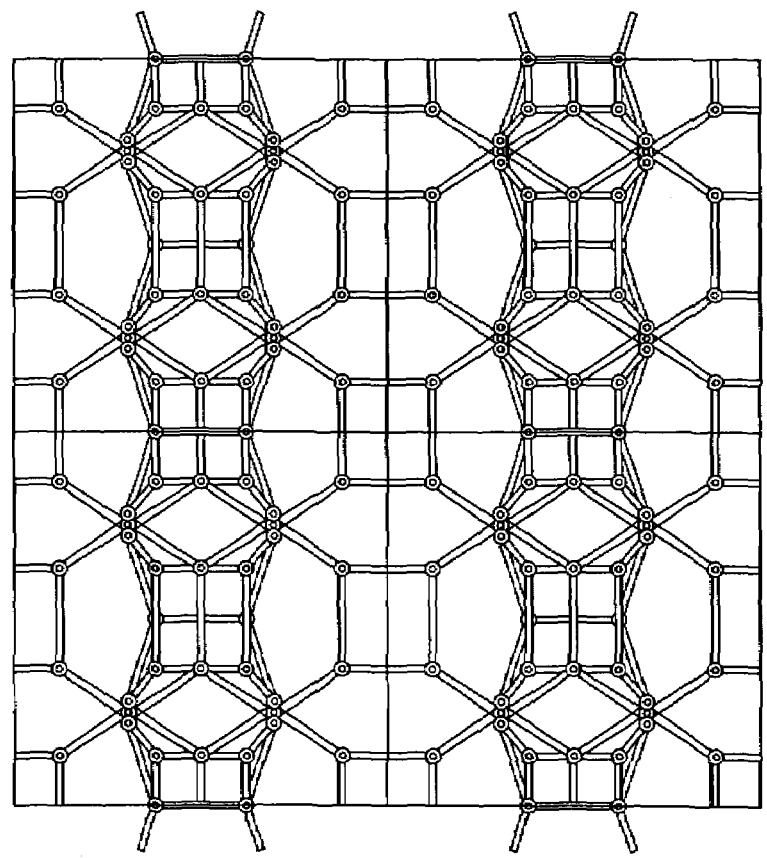

The term "aromatics conversion", as used herein, shall mean the production of aromatics by the conversion of non-aromatic hydrocarbons to aromatic compounds. The term "aromatics conversion", as used herein, shall also include the conversion of feedstock comprising aromatic compounds to a product comprising aromatic compounds which differ from said feedstock. The term "aromatics conversion", as used herein, shall further include the selective adsorption of aromatic hydrocarbons, e.g., alkyl substituted benzenes such as xylenes, for the purpose of separating various isomers of the aromatic hydrocarbons, e.g., separation of para-xylene from ortho-xylene and meta-xylene.

The synthetic porous crystalline material ITQ-13 is described in copending U.S. patent application Ser. No. 09/866,907, which is hereby incorporated by reference. ITQ-13 is a single crystalline phase that has a unique 3-dimensional channel system comprising three sets of channels. In particular, ITQ-13 comprises a first set of generally parallel channels each of which is defined by a 10-membered ring of tetrahedrally coordinated atoms, a second set of generally parallel channels which are also defined by 10-membered rings of tetrahedrally coordinated atoms and which are perpendicular to and intersect with the channels of the first set, and a third set of generally parallel channels which intersect with the channels of said first and second sets and each of which is defined by a 9-membered ring of tetrahedrally coordinated atoms. The first set of 10-ring channels each has cross-sectional dimensions of about 4.8 Å by about 5.5 Å, whereas the second set of 10-ring channels each has cross-sectional dimensions of about 5.0 Å by about 5.7 Å. The third set of 9-ring channels each has cross-sectional dimensions of about 4.0 Å by about 4.9 Å.

The structure of ITQ-13 may be defined by its unit cell, which is the smallest structural unit containing all the structural elements of the material. Table 1 lists the positions of each tetrahedral atom in the unit cell in nanometers; each tetrahedral atom is bonded to an oxygen atom that is also bonded to an adjacent tetrahedral atom. Since the tetrahedral atoms may move about due to other crystal forces (presence of inorganic or organic species, for example), a range of ±0.05 nm is implied for each coordinate position.

TABLE 1

| T1 | 0.626 | 0.159 | 0.794 |
|---|---|---|---|
| T2 | 0.151 | 0.151 | 0.478 |
| T3 | 0.385 | 0.287 | 0.333 |
| T4 | 0.626 | 0.158 | 0.487 |
| T5 | 0.153 | 0.149 | 0.781 |
| T6 | 0.383 | 0.250 | 1.993 |
| T7 | 0.473 | 0.153 | 0.071 |
| T8 | 0.469 | 0.000 | 1.509 |
| T9 | 0.466 | 0.000 | 1.820 |
| T10 | 0.626 | 0.979 | 0.794 |
| T11 | 1.100 | 0.987 | 0.478 |
| T12 | 0.867 | 0.851 | 0.333 |
| T13 | 0.626 | 0.980 | 0.487 |
| T14 | 1.099 | 0.989 | 0.781 |
| T15 | 0.869 | 0.888 | 1.993 |
| T16 | 0.778 | 0.985 | 0.071 |
| T17 | 0.783 | 0.000 | 1.509 |
| T18 | 0.785 | 0.000 | 1.820 |
| T19 | 0.151 | 0.987 | 0.478 |
| T20 | 0.385 | 0.851 | 0.333 |
| T21 | 0.153 | 0.989 | 0.781 |
| T22 | 0.383 | 0.888 | 1.993 |
| T23 | 0.473 | 0.985 | 0.071 |
| T24 | 1.100 | 0.151 | 0.478 |
| T25 | 0.867 | 0.287 | 0.333 |
| T26 | 1.099 | 0.149 | 0.781 |
| T27 | 0.869 | 0.250 | 1.993 |
| T28 | 0.778 | 0.153 | 0.071 |
| T29 | 0.626 | 0.728 | 1.895 |
| T30 | 0.151 | 0.720 | 1.579 |
| T31 | 0.385 | 0.856 | 1.433 |
| T32 | 0.626 | 0.727 | 1.588 |
| T33 | 0.153 | 0.718 | 1.882 |
| T34 | 0.383 | 0.819 | 0.893 |
| T35 | 0.473 | 0.722 | 1.171 |
| T36 | 0.469 | 0.569 | 0.409 |
| T37 | 0.466 | 0.569 | 0.719 |
| T38 | 0.626 | 0.410 | 1.895 |
| T39 | 1.100 | 0.418 | 1.579 |
| T40 | 0.867 | 0.282 | 1.433 |
| T41 | 0.626 | 0.411 | 1.588 |
| T42 | 1.099 | 0.420 | 1.882 |
| T43 | 0.869 | 0.319 | 0.893 |
| T44 | 0.778 | 0.416 | 1.171 |
| T45 | 0.783 | 0.569 | 0.409 |
| T46 | 0.785 | 0.569 | 0.719 |
| T47 | 0.151 | 0.418 | 1.579 |
| T48 | 0.385 | 0.282 | 1.433 |
| T49 | 0.153 | 0.420 | 1.882 |
| T50 | 0.383 | 0.319 | 0.893 |
| T51 | 0.473 | 0.416 | 1.171 |
| T52 | 1.100 | 0.720 | 1.579 |
| T53 | 0.867 | 0.856 | 1.433 |
| T54 | 1.099 | 0.718 | 1.882 |
| T55 | 0.869 | 0.819 | 0.893 |
| T56 | 0.778 | 0.722 | 1.171 |

ITQ-13 can be prepared in essentially pure form with little or no detectable impurity crystal phases and has an X-ray diffraction pattern which is distinguished from the patterns of other known as-synthesized or thermally treated crystalline materials by the lines listed in Table 2 below.

TABLE 2

| d (Å) | Relative Intensities (I) |
|---|---|
| 12.46 ± 0.2 | w–vs |
| 10.97 ± 0.2 | m–vs |
| 10.12 ± 0.2 | vw–w |
| 8.25 ± 0.2 | vw |
| 7.87 ± 0.2 | w–vs |
| 5.50 ± 0.15 | w–m |
| 5.45 ± 0.15 | vw |
| 5.32 ± 0.15 | vw–w |
| 4.70 ± 0.15 | vw |
| 4.22 ± 0.15 | w–m |
| 4.18 ± 0.15 | vw–w |
| 4.14 ± 0.15 | w |
| 3.97 ± 0.1 | w |
| 3.90 ± 0.1 | vw–m |
| 3.86 ± 0.1 | m–vs |
| 3.73 ± 0.1 | m–vs |
| 3.66 ± 0.1 | m–s |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units, and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

Preferably, the synthetic porous crystalline material has an X-ray diffraction pattern including d-spacing and relative intensity values substantially as set forth in Table 2.

ITQ-13 has a composition involving the molar relationship:

$$X_2O_3:(n)YO_2,$$

wherein X is a trivalent element, such as aluminum, boron, iron, indium, and/or gallium, preferably boron; Y is a tetravalent element such as silicon, tin, titanium and/or germanium, preferably silicon; and n is at least about 5, such as about 5 to infinity, and usually from about 40 to about infinity. It will be appreciated from the permitted values for n that ITQ-13 can be synthesized in totally siliceous form in which the trivalent element X is absent or essentially absent.

Processes for synthesizing ITQ-13 employ fluorides, in particular HF, as a mineralizing agent and hence, in its as-synthesized form, ITQ-13 has a formula, on an anhydrous basis and in terms of moles of oxides per n moles of $YO_2$, as follows:

$$(0.2–0.4)R: X_2O_3:(n)YO_2:(0.4–0.8)F$$

wherein R is an organic moiety. The R and F components, which are associated with the material as a result of their presence during crystallization, are easily removed by post-crystallization methods hereinafter more particularly described.

To the extent desired and depending on the $X_2O_3/YO_2$ molar ratio of the material, any cations in the as-synthesized ITQ-13 can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

The as-synthesized ITQ-13 may be subjected to treatment to remove part or all of any organic constituent used in its synthesis. This is conveniently effected by thermal treatment in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

Prior to use in the process of the invention, the ITQ-13 is preferably dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the ITQ-13 in a vacuum, but a longer time is required to obtain a sufficient amount of dehydration.

The silicate and borosilicate forms of ITQ-13 can be prepared from a reaction mixture containing sources of water, optionally an oxide of boron, an oxide of tetravalent element Y, e.g., silicon, a directing agent (R) as described below and fluoride ions, said reaction mixture having a composition, in terms of mole ratios of oxides, within the following ranges:

| Reactants | Useful | Preferred |
|---|---|---|
| $YO_2/B_2O_3$ | at least 5 | At least 40 |
| $H_2O/YO_2$ | 2–50 | 5–20 |
| $OH^-/YO_2$ | 0.05–0.7 | 0.2–0.4 |
| $F/YO_2$ | 0.1–1 | 0.4–0.8 |
| $R/YO_2$ | 0.05–0.7 | 0.2–0.4 |

The organic directing agent R used herein is the hexamethonium [hexamethylenebis(trimethylammonium)] dication and preferably is hexamethonium dihydroxide. Hexamethonium dihydroxide can readily be prepared by anion exchange of commercially available hexamethonium bromide.

Crystallization of ITQ-13 can be carried out at either static or stirred conditions in a suitable reactor vessel, such as for example, polypropylene jars or Teflon®-lined or stainless steel autoclaves, at a temperature of about 120° C. to about 160° C. for a time sufficient for crystallization to occur at the temperature used, e.g., from about 12 hours to about 30 days. Thereafter, the crystals are separated from the liquid and recovered.

It should be realized that the reaction mixture components can be supplied by more than one source. The reaction mixture can be prepared either batch-wise or continuously. Crystal size and crystallization time of the new crystalline material will vary with the nature of the reaction mixture employed and the crystallization conditions.

Synthesis of ITQ-13 may be facilitated by the presence of at least 0.01 percent, preferably 0.10 percent and still more preferably 1 percent, seed crystals (based on total weight) of crystalline product.

The ITQ-13 used in the process of the invention is preferably an aluminosilicate or boroaluminosilicate and more preferably has a silica to alumina molar ratio of less than about 1000. Aluminosilicate ITQ-13 can readily be produced from the silicate and borosilicate forms by post-synthesis methods well-known in the art, for example by ion exchange of the borosilicate material with a source of aluminum ions.

The "alpha value" refers to the acid activity of a catalyst, which is exemplified by its catalytic cracking activity. The alpha test is described in U.S. Pat. No. 3,354,078 and in *The Journal of Catalysis*, Vol. 4, pp. 522–529 (1965); Vol. 6, p. 278 (1966); and Vol. 61, p. 395 (1980), each incorporated herein by reference as to that description. Usually, the catalyst containing the crystalline ITQ-13 will have an alpha value in the range of from about 1 to about 900, and, more preferably, in the range of from about 2 to about 400.

The crystalline ITQ-13 may be employed in combination with a binder material resistant to the temperature and other conditions employed in aromatic conversion processes. Such binder materials include synthetic or naturally occurring substances as well as inorganic materials such as clay, silica, alumina, and/or metal oxides. The latter may be either naturally occurring or in the form of gelatinous precipitates or gels including mixtures of silica and metal oxides. Naturally occurring clays, which can be composited with the ITQ-13, include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid, treatment or chemical modification.

In addition to the foregoing materials, the ITQ-13 may be composited with a porous matrix material, such as active carbon, carbon fiber, alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The ITQ-13 may also be composited with amorphous mesoporous molecular sieves such as MCM-41 and MCM-48. Further, the ITQ-13 may be composited with crystalline microporous molecular sieve material. Examples of such materials are disclosed in PCT Publication 96/16004, which is hereby incorporated by reference.

The relative proportions of ITQ-13 component and binder material will vary widely with the ITQ-13 content ranging from between about 1 to about 99 percent by weight, more preferably in the range of about 10 to about 70 percent by weight of ITQ-13 component, and still more preferably from about 20 to about 50 percent.

The catalyst may also include at least one hydrogenation/dehydrogenation metal. Reference to the hydrogenation/dehydrogenation metal or metals is intended to encompass such metal or metals in the elemental state (i.e. zero valent) or in some other catalytically active form such as an oxide, sulfide, halide, carboxylate and the like. Such metals are known to persons skilled in the art and include, for example, one or more metals, and metals of Groups IIIA, IVA, VA, VIA, VIIA, VIIIM, IB, IIB, IIIB, IVB, VB, VIB, and VB of the Periodic Table of the Elements. Examples of suitable metals include Group VIII metals (i.e., Pt. Pd, Ir, Rh, Os, Ru, Ni, Co and Fe), Group IVA metals (i.e., Sn and Pb), Group VA metals (i.e., Sb and Bi), and Group VIIB metals (i.e., Mn, Tc and Re). Noble metals (i.e., Pt, Pd, Ir, Rh, Os and Ru) are sometimes preferred.

The amount of metal present in the catalyst will be an effective amount which will generally be from about 0.001 to about 20 percent by weight and, preferably 0.05 to 3.0 percent by weight. The amount will vary with the nature of the metal, less of the highly active metals, particularly platinum, being required than of the less active metals.

ITQ-13 can be used as catalysts for a variety of aromatics conversion processes. Examples of aromatics conversion processes where aromatic compounds are converted to different aromatic compounds include, as non-limiting examples, the following:

(A) The isomerization of dialkyl substituted benzenes, e.g., xylenes. Typical reaction conditions including a temperature from about 230° C. to about 510° C., a pressure of from about 1 atmosphere to about 50 atmospheres, a weight hourly space velocity of from about 0.1 $hr^{-1}$ to about 200 $hr^{-1}$ and a hydrogen/hydrocarbon mole ratio of from 0 (no added hydrogen) to about 100.

(B) The disproportionation of monoalkyl substituted benzenes, e.g., disproportionation of toluene to benzene and xylenes. Typical reaction conditions including a temperature of from about 200° C. to about 760° C., a pressure of from about atmospheric to about 60 atmospheres and a weight hourly space velocity of from about 0.08 $hr^{-1}$ to about 20 $hr^{-1}$.

(C) The alkylation of aromatic compounds, e.g. benzene and $C_7$ and $C_8$ alkylbenzenes, in the presence of an alkylating agent, e.g., olefins, formaldehyde, alkyl halides, and oxygenates, e.g., ethers, and alcohols. Typical reaction condition include a temperature of from about 340° C. to about 500° C., a pressure of from about atmospheric to about 200 atmospheres, a weight hourly space velocity of from about 2 $hr^{-1}$ to about 2000 $hr^{-1}$ and an aromatic hydrocarbon/alkylating agent mole ratio of from about 1/1 to about 20/1.

(D) The transalkylation of aromatic compounds in the presence of polyalkylaromatic compounds. Typical reaction conditions include a temperature of from about 340° C. to about 600° C., a pressure of from about atmospheric to about 200 atmospheres, a weight hourly space velocity of from about 10 $hr^{-1}$ to about 1000 $hr^{-1}$ and an aromatic hydrocarbon/polyalkylaromatic hydrocarbon mole ratio of from about 1/1 to about 16/1.

(E) The dealkylation of alkylaromatic compounds. In the case of ethylbenzene, the ethylbenzene can be converted to benzene and ethane. Typical reaction conditions including a temperature from about 230° C. to about 510° C., a pressure of from about 1 atmosphere to about 50 atmospheres, a weight hourly space velocity of from about 0.1 $hr^{-1}$ to about 200 $hr^{-1}$ and a hydrogen/hydrocarbon mole ratio of from 0 (no added hydrogen) to about 100.

(F) The isomerization of ethylbenzene to form xylenes. Exemplary conditions include a temperature from about 300° C. to about 550° C., a pressure of from about 50 to 500 psig, and a LHSV of from about 1 to about 20.

(G) The adsorption of xylenes for the purpose of separation of the isomers.

(H) The isomerization of dialkylnaphthalene, e.g., dimethylnaphthalene, to form a mixture of isomers. Of the dimethylnapthalene isomers, 2,6-dimethylnapthalene is a key intermediate in the production of 2,6-napthalenedicarboxylic acid, a valuable monomer for specialty polyester manufacture. Typical reaction conditions including a temperature from about 230° C. to about 510° C., a pressure of from about 1 atmosphere to about 50 atmospheres, a weight hourly space velocity of from about 0.1 $hr^{-1}$ to about 200 $hr^{-1}$ and a hydrogen/hydrocarbon mole ratio of from 0 (no added hydrogen) to about 100.

(I) The disproportionation of mono-alkyl substituted naphthalenes, e.g., disproportionation of mono-methyl naphthalene to dimethylnaphthalene and naphthalene. Typical reaction conditions including a temperature of from about 200° C. to about 760° C., a pressure of from about atmospheric to about 60 atmospheres and a weight hourly space velocity of from about 0.08 $hr^{-1}$ to about 20 $hr^{-1}$.

(J) The oxidation of alkyl substituted aromatic compounds, e.g., conversion of para-xylene to para-terephthalic acid and the conversion of cumene to phenol and acetone and the conversion of 2,6-dimethylnapthalene to 2,6-napthalenedicarboxylic acid.

Non-limiting examples of aromatic compounds that can be converted to different aromatic compounds by the process of the present invention include the following:

(A) monocyclic alkylaromatic compounds represented by the formula:

I wherein:
R, $R^1$, and $R^2$ are independently selected from the group consisting of hydrogen and an alkyl or alkenyl group having 1 to about 12 carbon atoms, and, preferably 1 to 4 carbon atoms; and, (B) bicyclic alkylaromatic compounds represented by the formula:

II

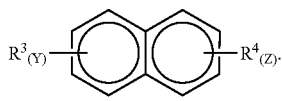

wherein:
$R^3$ and $R^4$ are independently selected from the group consisting of hydrogen and an alkyl or alkenyl group having 1 to about 12 carbon atoms, and, preferably 1 to 4 carbon atoms:
Y is an integer of from 0 to 2; and
Z is an integer of from 0 to 2.

Examples of R, $R^1$, $R^2$, $R^3$, and $R^4$ include straight or branch chained alkyl and alkenyl groups. Examples of such groups include methyl, ethyl, ethylene, n-propyl, isopropyl, propylene, n-butyl, isobutyl, butylene or any combination thereof. The preferred group is methyl.

Examples of monocyclic alkylaromatic compounds corresponding to formula I include, for example, benzene, toluene ethylbenzene, styrene, xylenes such as para-xylene, ortho-xylene, and meta-xylene, diethylbenzenes such as 1,4diethylbenzene, 1,2-diethylbenzene, and 1,3-diethylbenzene, trimethylbenzenes such as mesitylene (1,3,5-trimethylbenzene), hemimellitene (1,2,3-trimethylbenzene), and pseudocumene (1,2,4-trimethylbenzene), ethyltoluenes, triethylbenzenes such as 1,3,5-triethylbenzene, methylpropylbenzenes, ethylpropylbenzenes, dipropylbenzenes, diisopropylbenzenes, triisopropylbenzenes, and the like.

Examples of bicyclic alkylaromatic compounds corresponding to formular II include 1-methylnaphthalene, 2-methylnaphthalene, dialkylnaphthalenes such as 1,2-dimethylnaphthalene, 1,2-diethylnaphthalene 2,3-dimethylnaphthalene, 2,3-dipropylnaphthalene 2,6-dimethylnaphthalene, 2,6-dibutyl-naphthalene, and the like.

Examples of aromatic compounds to be converted and resulting products are shown below in the table:

| Aromatics To Undergo Conversion | Non-Aromatic Reactants | Aromatic Product |
| --- | --- | --- |
| Benzene | Ethylene | Ethylbenzene |
| Toluene | Methanol | Xylene isomers |
| Xylene | — | Different |

| Aromatics To Undergo Conversion | Non-Aromatic Reactants | Aromatic Product |
| --- | --- | --- |
| isomers, e.g., 9:73:18 wt. ratio of para:meta:ortho | | combination of xylene isomers, e.g. 23:57:20 wt. ratio of para:meta:ortho |
| Toluene | — | Benzene and xylenes |
| Benzene | Propylene | Cumene and diisopropylbenzene |
| Toluene | Propylene | Cymene isomers |

Examples of aromatics conversion processes where non-aromatic compounds are converted to aromatic compounds include, as non-limiting examples, the following:

(A) The conversion of light paraffins to aromatics and olefins. Typical reaction conditions include a temperature from about 375° C. to about 760° C. and a pressure from about 10 to about 2000 psig.

(B) The conversion of light olefins to aromatics. Exemplary reaction conditions include a temperature from about 175° C. to about 760° C. and a pressure from about 100 to about 2000 psig (C) The conversion of naphtha, e.g., $C_6$–$C_{10}$, and similar mixtures to highly aromatic mixtures. Thus, normal and slightly branched chained hydrocarbons, preferably having a boiling range above about 40° C., and less than about 200° C., can be converted to products having a substantial higher octane aromatics content. Typical reactions include a temperature in the range of from about 400° C. to 600° C., preferably 480° C. to 550° C., a pressure in the range from atmospheric to 40 bar, and liquid hourly space velocities (LHSV) ranging from 0.1 to 15.

(D) The dehydrogenation of cycloaliphatics having 6 member rings. Typical reaction conditions include a temperature of from about 300° C. to about 700° C., a pressure of from about 0.1 to about 10 atmospheres, a weight hourly space velocity of from about 0.1 $hr^{-1}$ to about 20 $hr^{-1}$.

(E) The conversion of alcohols, e.g., methanol, or ethers, dimethylether, or mixtures thereof to aromatics. Typical reaction conditions include a temperature of from about 275° C. to about 600° C., a pressure of from about 0.5 to about 50 atmospheres, a LHSV of from about 0.5 $hr^{-1}$ to about 50 $hr^{-1}$. Examples of such processes are disclosed in U.S. Pat. No. 4,088,706, which is hereby incorporated by reference.

(F) The dehydration of alcohols to form aromatics, such as the dehydration of cyclohexane-triol to form benzene.

Reaction conditions for aromatics conversion include, in general, a temperature of from about 200° C. to about 760° C., a pressure of from about atmospheric to about 200 atmospheres, and a weight hourly space velocity of from about $0.08^{-1}$ to about 2000 $hr^{-1}$.

The catalyst comprising the ITQ-13 can be selectivated with a selectivating agent when used in aromatics conversion, e.g., toluene disproportionation, xylenes isomerization, aromatics alkylation, light olefin conversion to aromatics, and the like. The term "selectivating agent" is used herein to indicate substances which will increase the shape-selectivity (e.g., para-selectivity) of the ITQ-13. The catalyst can be selectivated by treating the surface of the catalyst with compounds of phosphorus and/or various metal oxides such as alkaline earth metal oxides, e.g., calcium oxide, magnesium oxide, etc. rare earth metal oxides, lanthanum oxide, and other metal oxides such as boron oxide, titania, antimony oxide, and manganese oxide. The catalyst can also be selectivated by depositing coke on the catalyst.

Furthermore, selectivation can be accomplished using organosilicon compounds. The organosilicon compounds may comprise polysiloxane including silicone and siloxanes, and a silane including disilanes and alkoxysilanes.

Organosilicon compounds include siloxanes which can be represented by the general formula:

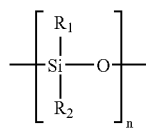

wherein $R_1$ is hydrogen, halogen, hydroxyl, alkyl, halogenated alkyl, aryl aralkyl, halogenated aralkyl, alkaryl, or halogenated alkaryl. The hydrocarbon substituents generally contain from 1 to about 10 carbon atoms, preferably methyl, ethyl, or phenyl groups. $R_2$ is selected from the same group as $R_1$, and n is an integer of at least 2 and generally in the range of 3 to about 1000. The molecular weight of the silicone compound employed is generally between about 80 to about 20,000 and preferably about 150 to about 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylphenyl silicone, methylvinyl silicone and ethylvinyl silicone. The silicone compound need not be linear but may be cyclic as for example hexamethyl cyclotrisiloxane, octamethyl cyclotetrasiloxane, hexaphenyl cyclotrisiloxane, and octaphenyl cyclotetrasiloxane. Mixtures of these compounds may also be used as well as silicones with other functional groups.

Other silicon compounds, including silanes, alkoxy silanes, such as tetramethoxy silane, can also be utilized. These useful silicon-containing selectivating agents include silanes characterized by the general formula:

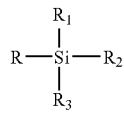

wherein R, $R_1$, $R_2$ and $R_3$ are independently selected from the group consisting of hydrogen, hydroxyl, halogen, alkyl, halogenated alkyl, alkoxy, aryl, halogenated alkaryl groups. Mixtures of these compounds can also be used.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich.

Examples of suitable carriers for the selectivating silicon compound include linear, branched, and cyclic alkane having five or more carbons. In the methods of the present invention it is preferred that the carrier be a linear, branched, or cyclic alkane having a boiling point greater than about 70° C., and most preferably containing 6 or more carbons. Optionally, mixtures of low volatility organic compounds, such as hydrocracker recycle oil, can be employed as carriers. The most preferred low volatility hydrocarbon carriers of selectivating agents are decane and dodecane.

The catalyst can be selectivated by single or multiple treatments with a liquid organosilicon compound in a liquid carrier, each treatment being followed by calcination of the treated material in an oxygen containing atmosphere. The catalyst can also be selectivated with both silica and coke.

The process of the present invention finds particular application in the vapor phase disproportionation of toluene. Such vapor phase disproportionation comprises contacting a feed stream containing toluene under disproportionation conditions with a catalyst comprising ITQ-13 to yield a product mixture which comprises a mixture of unreacted (unconverted) toluene and benzene and xylene.

In a preferred embodiment, the catalyst is selectivated to produce enhanced amounts of para-xylene. When coke is the selectivating agent, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke.

The disproportionation is usually carried out at conditions which include a temperature between about 375° C. and 550° C., more preferably between about 400° C. and 485° C., at a hydrogen to toluene mole ratio of from 0 to about 10, preferably between about 0.1 and 5 and more preferably from about 0.1 to 1, at a pressure between about 1 atmosphere and 100 atmospheres and utilizing WHSV of between about 0.5 and 50.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

The process of the present invention finds particular application in a process for the production of alkylated aromatic compounds, e.g., xylenes, by alkylating aromatic compounds, e.g., benzene or toluene, with an alkylating agent in the presence of a catalyst comprising ITQ-13. Examples of suitable aromatic compounds include benzene, toluene, ortho-xylene, metaxylene, para-xylene, ethylbenzene, ortho-ethyltoluene, meta-ethyltoluene, para-ethyltoluene, 1,2,3-trimethylbenzene, 1,2,4-trimethylbenzene, and 1,3,5-trimethylbenzene. Higher molecular weight alkylaromatic compounds are also suitable.

Alkylating agents suitable for use in the present invention are olefins, alcohols, alkenes, alkynes, aldehydes, ethers, acetylenes, and any other acyclic compounds having at least one reactive alkyl group. Suitable alcohols include methanol, ethanol, n-propoanol, and isopropanol. The olefins can be $C_2$ to $C_{20}$ olefins, preferably $C_2$-$C_{12}$ olefins, including normal and branched forms thereof. For example, suitable olefins are ethylene, propylene, butylene, isobutylene, 1-pentene, 1-hexene, 2-hexene, cyclohexene, methyl cyclohexene, 2,3-dimethyl-1-pentene, 1-octene, diisobutylene, 1-nonene and 1-decene, dodecene and the like.

When the aromatic compound to be alkylated is toluene and the alkylating agent is methanol, preferably at least 60% of the methanol is converted to form xylenes. Methanol utilization is determined by (moles of methanol converted)/(moles of xylene formed—moles of benzene formed). Benzene is subtracted to account for any xylene formed by the disproportionation of toluene to xylene plus benzene.

Both toluene disproportation and aromatics alkylation can be carried out by reactive distillation. The term "reactive distillation", as used herein, means the production of desired product, e.g., xylenes, while concurrently removing the product from a reaction zone. The term "reaction/distillation column", as used herein, means a column in which the aromatics to undergo conversion, e.g., toluene, are contacted in the presence of a catalyst comprising ITQ-13 to produce the desired product, e.g., xylenes, and from which the desired product is withdrawn.

The reactive distillation reaction is preferably carried out in a reaction/distillation column. In this embodiment, the aromatics to undergo conversion, e.g., toluene, are usually fed continuously to the reaction/distillation column and the resulting product is continuously withdrawn from the bottom of the reaction/distillation column. In this embodiment, the continuous removal of the desired product from the reaction/distillation column increases the extent of reaction achieved within the column, thus providing very high conversion along with low by-product formation. Equipment suitable for carrying out reactive distillation is disclosed in PCT Publication No. WO 99/38823, which is hereby incorporated by reference.

The present invention also finds particular application in a process for isomerizing one or more xylene isomers in a $C_8$ aromatic feed to obtain ortho-,meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. Ethylbenzene in the feed is either removed from the stream or is converted during the process to xylenes or to benzene which are easily separated by distillation. The isomerate is blended with fresh feed and the combined stream is distilled to remove heavy and light by-products. The resultant $C_8$ aromatics stream is then recycled to repeat the cycle.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 0.1 to 30.0 moles of hydrogen per mole of alkylbenzene.

The xylene isomerization reaction is usually be carried out in a fixed bed reactor containing the catalyst comprising ITQ-13. The xylene isomerization reaction can also be carried out in sequential beds using two catalysts. In this embodiment, each catalyst is in a separate bed or one of the catalysts forms one part of a bed while the second catalyst form the remaining part of the bed and is located downstream with respect to the first catalyst. The first catalyst is used primarily for ethylbenzene conversion while the second catalyst is used primarily for xylene isomerization. In this embodiment, the catalyst comprising ITQ-13 is preferably the second catalyst and the first catalyst is one that is specifically adapted for ethylbenzene conversion, e.g., ZSM-5 with hydrogenation metal. In this embodiment, the catalyst comprising ITQ-13 will preferably comprise from about 10 percent to about 90 percent of the bed volume.

When used to isomerize feeds containing ethylbenzene, the catalyst will preferably contain at least one hydrogenation metal.

The process of the present invention finds particular application in the transalkylation of polyalkylaromatic compounds. The feed used in the process will usually comprise one or more aromatic compounds containing at least 9 carbon atoms such as mesitylene (1,3,5-trimethylbenzene), durene (1,2,4,5-tetramethylbenzene), hemimellitene (1,3,3-trimethylbenzene), pseudocumene (1,2,4-trimethylbenzene), prehnitene (1,2,3,4-trimethylbenzene), isodurene (1,2,3,4-tetramethylbenzene), and 1,3,5-triethylbenzene. The feed can also be one containing multi-alkyl-aromatics, e.g., penta-methyl-benzene with naphthalene/methyl naphthatene. Preferably, the catalyst comprising ITQ-13 is combined with a hydrogenation component, such as platinum, palladium or rhenium, and is used in the catalytic conversion of $C_9+$ alkylaromatic compounds, either alone or in the presence of toluene and/or benzene, to produce xylenes. Such conversion is typically effected at a temperature of from about 650 to about 950° F. (340 to 510° C.), and preferably from about 750 to about 850° F. (400 to 450° C.), a pressure of from about 100 to about 600 psig (790 to 4240 kPa), and preferably from about 200 to about 500 psig (1480 to 3550 kPa), a weight hourly space velocity (WHSV) of between about 0.1 and about 200 $hr^{-1}$, and preferably between about 0.5 and about 20 $hr^{-1}$ and a hydrogen, $H_2$, to hydrocarbon, HC, molar ratio of between about 1 and about 5, and preferably from about 1 to about 3.

Typically, the reaction temperature will preferably range from about 340° C. to 500° C. to maintain at least a partial liquid phase, and the pressure will be preferably in the range of about 50 psig to 1,000 psig, preferably 300 psig to 600 psig, and the weight hourly space velocity will range from about 0.1 to 10.

The process of the present invention finds particular application for the production of aromatic compounds by the dehydrocyclo-oligomerization of aliphatic hydrocarbons containing 2 to about 6 carbon atoms. The aliphatic hydrocarbons may be open chain, straight chain, or cyclic and may be saturated, unsaturated, or a mixture of the above. Example of such hydrocarbons include ethane, ethylene, propane, propylene, n-butane, n-butenes, isobutane, isobutene, straight, branch, and cyclic pentane, pentenes, hexanes, and hexenes.

The dehydrocyclo-oligomerization conditions typically include a temperature of from about 350° C. to about 650° C., a pressure of from about 1 to about 20 atmospheres, a weight hourly space velocity (WHSV) of from about 0.2 to about 5. The catalyst used in the process will preferably contain gallium, zinc or mixtures thereof. Gallium or zinc may be incorporated into the ITQ-13 during synthesis or it may be exchanged or impregnated or otherwise incorporated into the ITQ-13 after synthesis. Preferably, 0.05 to 10, and most preferably 0.1 to 2.0 wt. % gallium or zinc is associated with the catalyst.

The process of the present invention finds particular application in a catalytic reforming process where $C_{6+}$ aliphatic hydrocarbons, preferably $C_6$–$C_8$ hydrocarbons, are converted to aromatic compounds. The process is carried out by passing the $C_{6+}$ aliphatic hydrocarbons under conversion conditions over a catalyst comprising ITQ-13 and a dehydrogenation metal such as a Group VIII metal such as platinum.

The ITQ-13 finds application for selectively separating aromatic hydrocarbons, e.g., alkyl substituted benzenes. An example of such a separation is $C_8$ isomer, e.g., para-xylene, separation. During the separation process, i.e., adsorption, the alkyl substituted benzenes, e.g., meta-xylene and/or ortho-xylene, may be converted to other isomers, e.g., para-xylene.

The adsorption process involves contacting a mixture containing the aromatic hydrocarbons, existing either as a gas, liquid or mixed phase, with the ITQ-13 for sufficient time to selectively adsorb the preferred aromatic hydrocarbon, e.g., alkyl substituted benzene, within the internal pore structure of the ITQ-13. The components of the mixture that are not adsorbed may be converted to adsorbable isomers during contact with the ITQ-13. The alkyl substituted benzene sorbed is thereafter recovered from the internal pore structure of the ITQ-13 by conventional desorbing techniques.

The temperature at which the adsorption process is conducted is not considered critical, so long as it is maintained below the desorption temperature of the adsorbed component. Preferably, the process is conducted at a temperature between ambient and about 150° C.

The following examples illustrate the invention:

EXAMPLE 1

Borosilicate ITQ-13 was synthesized from a gel having the following molar composition:

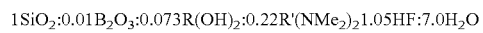

$1SiO_2:0.01B_2O_3:0.073R(OH)_2:0.22R'(NMe_2)_2 1.05HF:7.0H_2O$ where $R(OH)_2$ is hexamethonium dihydroxide, $R'(NMe_2)_2$ is N,N,N',N'-tetramethylhexane-1,6-diamine, and 4 wt % of the $SiO_2$ was added as ITQ-13 seeds to accelerate the crystallization. The hexamethonium dihydroxide employed in the gel was prepared by direct anionic exchange of commercially available hexamethonium dibromide using a resin, Amberlite IRN-78, as hydroxide source.

Figure 5:
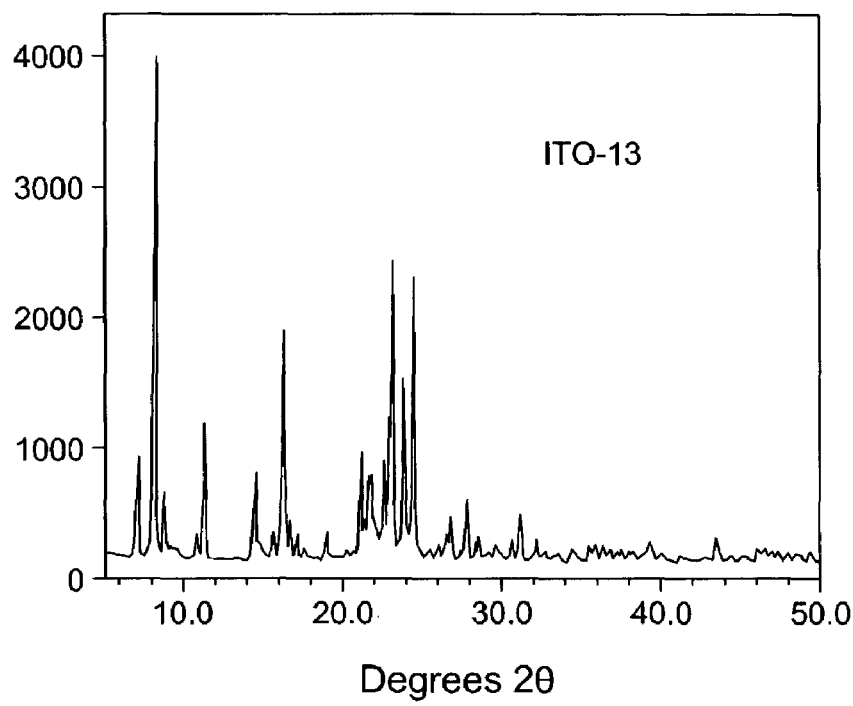
FIGS. 5 and 6 show the X-ray diffraction patterns of the as-synthesized and as-calcined boron-containing ITQ-13 product of Example 1.

The synthesis gel was prepared by adding 300 grams of silica (Aldrich-Syton HT-50) 3.09 grams of boric acid, 78.05 grams of 54.9 weight percent hexamethonium hydroxide solution, 93.9 grams of N,N,N',N'-tetramethylhexane-1,6-diamine, 109.4 grams of 48% weight percent HF, and 6.01 grams of ITQ-13 seeds to a PFA (perfluoroalkyoxyl-Teflon) bottle. The bottle was shaken for 30 minutes. The pH of the mixture was 7.3. The bottle was placed into a 2 liter autoclave and heated at 1° C./min to 135° C. and held at 135° C. for 21 days. At the end of this time the pH of the mixture was 7.1. The solid was then filtered, washed with water and dried at 80° C. to constant weight. The weight of the as-synthesized material was 151.9 grams. The X-ray diffraction pattern of the as-synthesized material is shown in FIG. 5.

Figure 6:
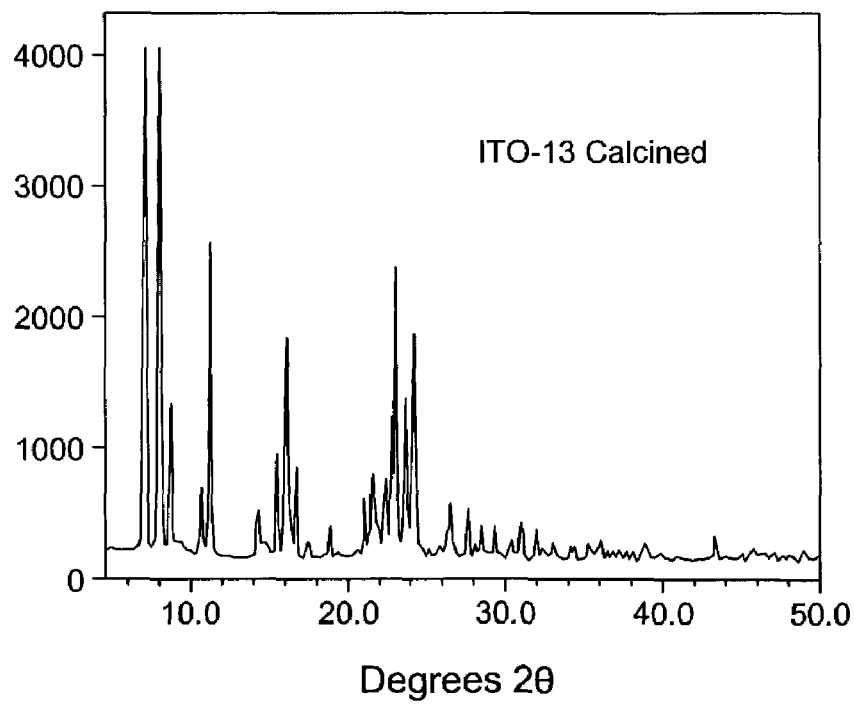

The as-synthesized material was calcined as a thin layer (~0.1 g/cm²) by ramping under $N_2$ 2° C./min to 230° C., holding 2 hours, ramping 2° C./min to 540° C., and holding 8 hours. The gas was then switched to dry air, and the sample held 8 hours at 540° C., then cooled under dry air. The X-ray diffraction pattern of the calcined material is shown in FIG. 6. Boron NMR Analysis indicated the boron content was 800 ppm.

Figure 7:
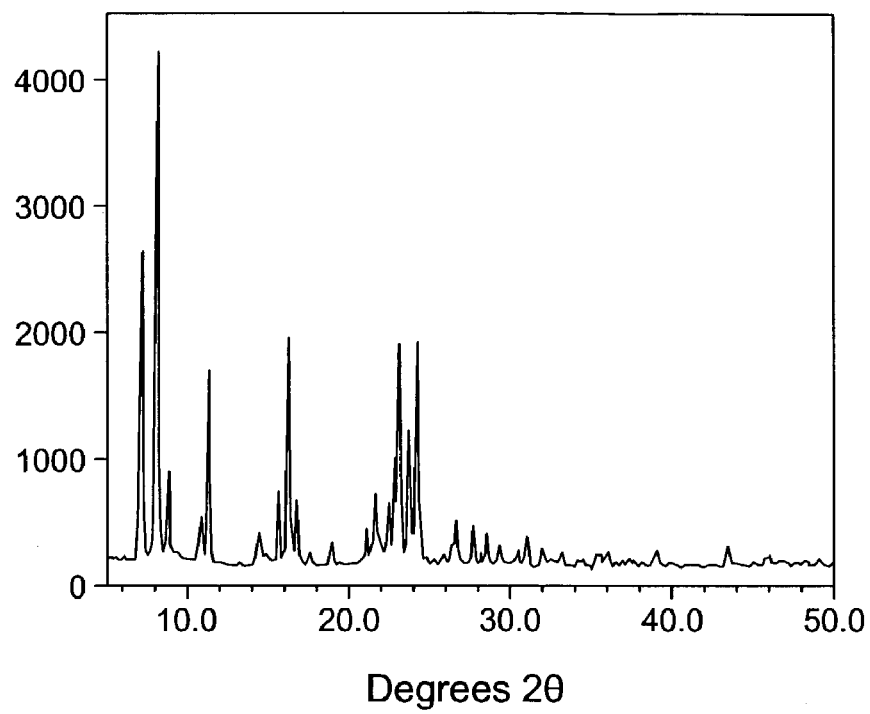
FIG. 7 shows the X-ray diffraction patterns of the aluminum-containing ITQ-13 product of Example 1.

The calcined material was converted from the boron to the aluminum form by mixing 45 grams of the calcined ITQ-13, 98.3 grams of $Al(NO_3)_3$ $H_2O$ and 540 grams $H_2O$ in a PFA bottle. The bottle was placed in a 2L autoclave and heated 1° C./min to 135° C., and held at 135° C. for 3 days. The product was filtered, washed with $H_2O$ until the wash water had a pH of greater than 5, then dried to constant weight at 80° C. The amount of material produced was 43 grams. The X-ray diffraction (FIG. 7) showed the calcined product to be ITQ-13 containing some 1–2 weight percent ZSM-50 impurity. Aluminum NMR analysis indicated the product to have a Si/Al atomic ratio of 800. The alpha value of the product was determined to be 2.

EXAMPLE 2

Xylenes isomerization was carried in a fixed-bed downflow reactor and over the aluminosilicate catalyst composition of Example 1 with a xylene feed that contained 98 weight percent of meta-xylene and 2 weight percent ortho-xylene. The conditions for the test included a temperature of 360° C., a pressure of 200 psig, a $H_2$ to hydrocarbon molar ratio of 2, and a weight hour space velocity of 2. The results of the tests are shown below in Table III.

TABLE III

| | Time on Stream, hr | | | | | | |
|---|---|---|---|---|---|---|---|
| | 4 | 6 | 10 | 12 | 16 | 18 | 24 |
| P-Xylene in Product, wt % | 23.5 | 23.5 | 23.5 | 23.4 | 23.4 | 23.4 | 23.4 |
| M-Xylene in Product, wt % | 54.8 | 54.9 | 55.0 | 55.1 | 55.1 | 55.2 | 55.2 |
| O-Xylene in Product, wt % | 21.3 | 21.3 | 21.3 | 21.2 | 21.3 | 21.2 | 21.2 |
| Total Xylenes, wt % | 99.7 | 99.7 | 99.7 | 99.8 | 99.8 | 99.8 | 99.8 |
| P-Xylene in Xylenes, wt % | 23.6% | 23.6% | 23.5% | 23.5% | 23.4% | 23.5% | 23.4% |
| Xylene loss, wt % | 0.1% | 0.1% | 0.0% | 0.0% | 0.0% | 0.0% | 0.0% |
| C5- Yield, wt % | 0.0 | 0.0 | 0.0 | 0.0 | 0.0 | 0.0 | 0.0 |
| C9+ Yield, wt % | 0.0 | 0.0 | 0.0 | 0.0 | 0.0 | 0.0 | 0.0 |

The data in Table III shows that xylenes isomerization using a catalyst comprising ITQ-13 produced a near equilibrium xylenes mixture with low xylenes loss and steady catalyst performance for 24 hours.

EXAMPLE 3

Xylenes isomerization/ethylbenzene conversion was carried in a fixed-bed downflow reactor and over the aluminosilicate catalyst composition of Example 1 with a xylene feed that contained 90 weight percent of meta-xylene and 10 weight percent ethylbenzene. The conditions used in the test were the same as Example 3. The results of the tests are shown in Table IV.

TABLE IV

| Time on Stream, hr | 10 | 20 | 30 |
|---|---|---|---|
| Temperature, C. | 360 | 400 | 450 |
| P-Xylene in Xylenes, wt % | 23.5% | 23.8% | 24.2% |
| EB Conversion, wt % | 2.8% | 9.8% | 27.9% |
| Total Xylenes, wt % | 89.8 | 88.8 | 85.4 |
| Toluene plus C9+, wt % | 0.6 | 0.9 | 2.6 |

The data in Table IV shows that xylenes isomerization using a catalyst comprising ITQ-13 produced a near equilibrium xylenes mixture with good ethylbenzene conversion.

EXAMPLE 4

Figure 8:
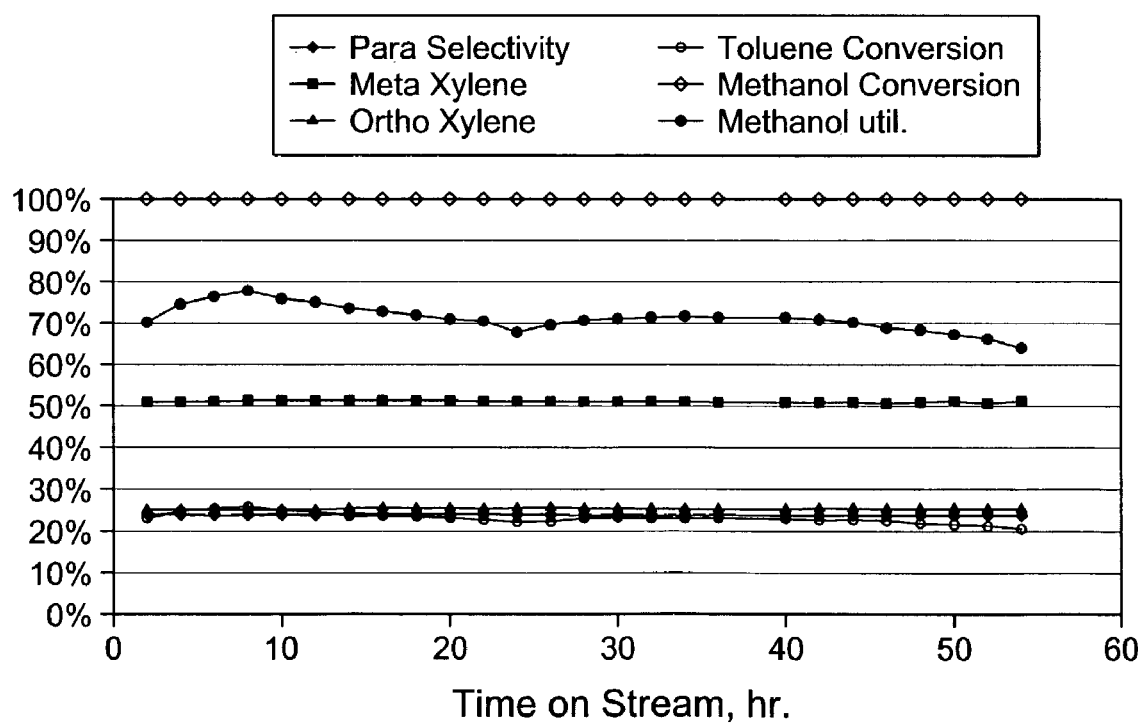
FIG. 8 is a graph depicting the test results of Example 4.

Toluene methylation was carried in a fixed-bed downflow reactor and over two grams of the aluminosilicate catalyst composition of Example 1. The test was carried out under the following operating conditions, unless otherwise noted: Temperature=600° C., Pressure=15 psig, $H_2$/hydrocarbon molar ratio=0.8, pure methanol and toluene feeds at 1:3 molar ratio, WHSV=3.9 h–1. The catalyst load was 2 g. The test results are graphically presented in FIG. 8.

The results show that the amount of toluene conversion was from 22–25 percent. Conversion of the methanol was 100 percent and 70 percent of this conversion was to xylenes. For a 1:3 molar feed mixture, the maximum conversion of toluene is expected to be about 33%.

EXAMPLE 5

Aluminosilicate ITQ-13 was synthesized from a gel having the following molar composition:

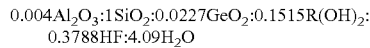

0.004Al$_2$O$_3$:1SiO$_2$:0.0227GeO$_2$:0.1515R(OH)$_2$:
0.3788HF:4.09H$_2$O where R(OH)$_2$ is hexamethonium dihydroxide and 3 wt % of the SiO$_2$ was added as ITQ-13 seeds to accelerate the crystallization. The hexamethonium dihydroxide employed in the gel was prepared by direct anionic exchange of commercially available hexamethonium dibromide using a resin, Amberlite IRN-78, as hydroxide source.

The synthesis gel was prepared by adding 119 grams of silica (Aldrich-Syton VN 3SP-PM), 4.71 grams of GeO$_2$ (Aldrich), 5.63 grams of aluminum nitrate nonahydrate (Aldrich), 129.2 grams of 54.9 weight percent hexamethonium hydroxide solution, 3.61 grams of ITQ-13 seeds, 68.9 grams of water, and 31.3 grams of 48% weight percent HF to a 1 liter PFA (perfluoroalkyoxyl-Teflon) bottle.

The bottle was shaken and then placed into a 2 liter autoclave at a pressure of 300 psi and heated at 1° C./min to 140° C. and held at 140° C. for 14 days. After cooling, the material was filtered, washed copiously with water and air dried under a heat lamp. The weight of the as-synthesized material was 136 grams.

Figure 9:
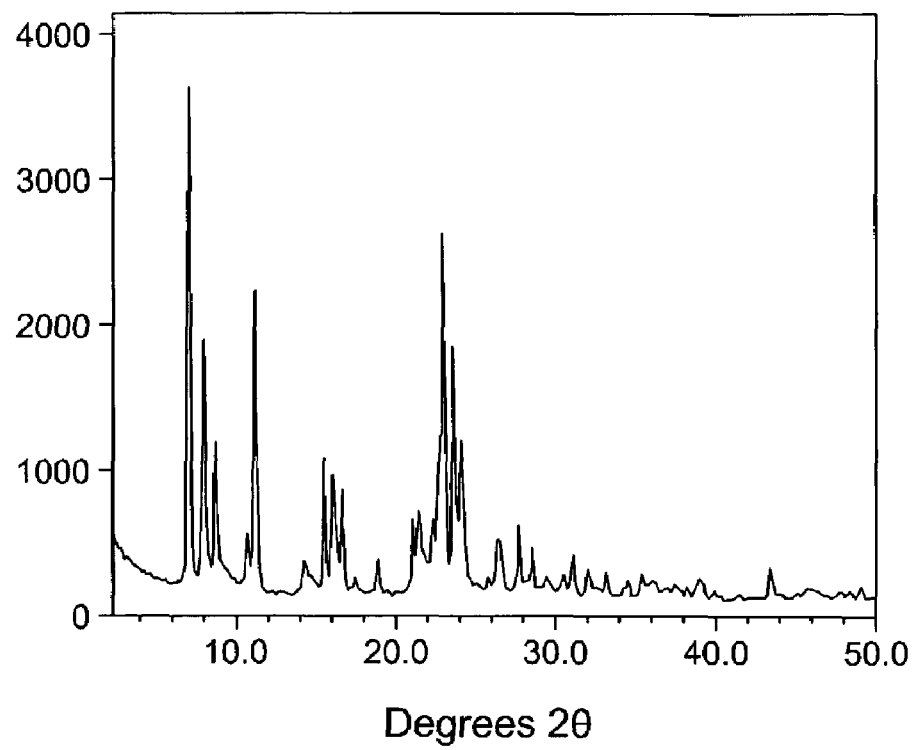
FIG. 9 shows the X-ray diffraction patterns of the aluminum-containing ITQ-13 product of Example 5.
Figure 10:
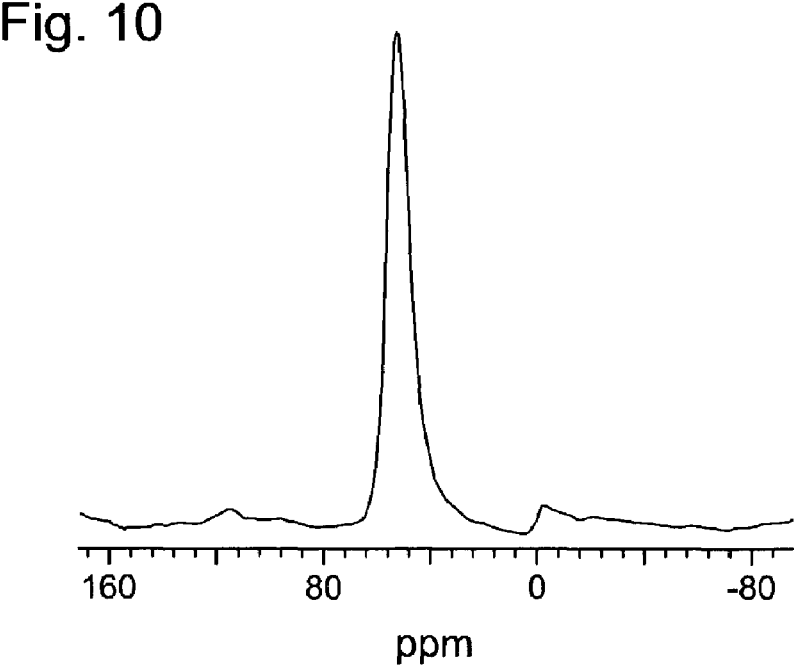
FIG. 10 shows the magic angle spinning aluminum NMR of the aluminum-containing ITQ-13 product of Example 5.

About 125 grams of the as-synthesized material was calcined as a thin layer by raising the temperature 1° C./min to 540° C. under dry air, holding 1 hour and then cooling to room temperature. After cooling, 104 grams of material was obtained. A sample of 45.1 grams was placed into a 1 liter PFA (perfluoroalkyoxyl-Teflon) bottle. Next, 532.5 grams of water and 98.46 grams of aluminum nitrate nonahydrate (Aldrich) were added to the bottle. The mixture was heated at 135° C., and three days. The resulting material was filtered, washed copiously with water and dried in an oven for 2 hours at 135° C., then cooled under dry air. The X-ray diffraction pattern of the material (FIG. 9) showed the product to be ITQ-13 substantially free of impurities. Magic angle spinning aluminum NMR (FIG. 10) showed an expected peak at 53.1 ppm relative to aluminum nitrate in aqueous solution. Integration of this NMR spectrum against a weighed standard material indicated the concentration of aluminum was 2800 ppm. The alpha value of the material was determined to be 39.

EXAMPLE 6

Figure 11:
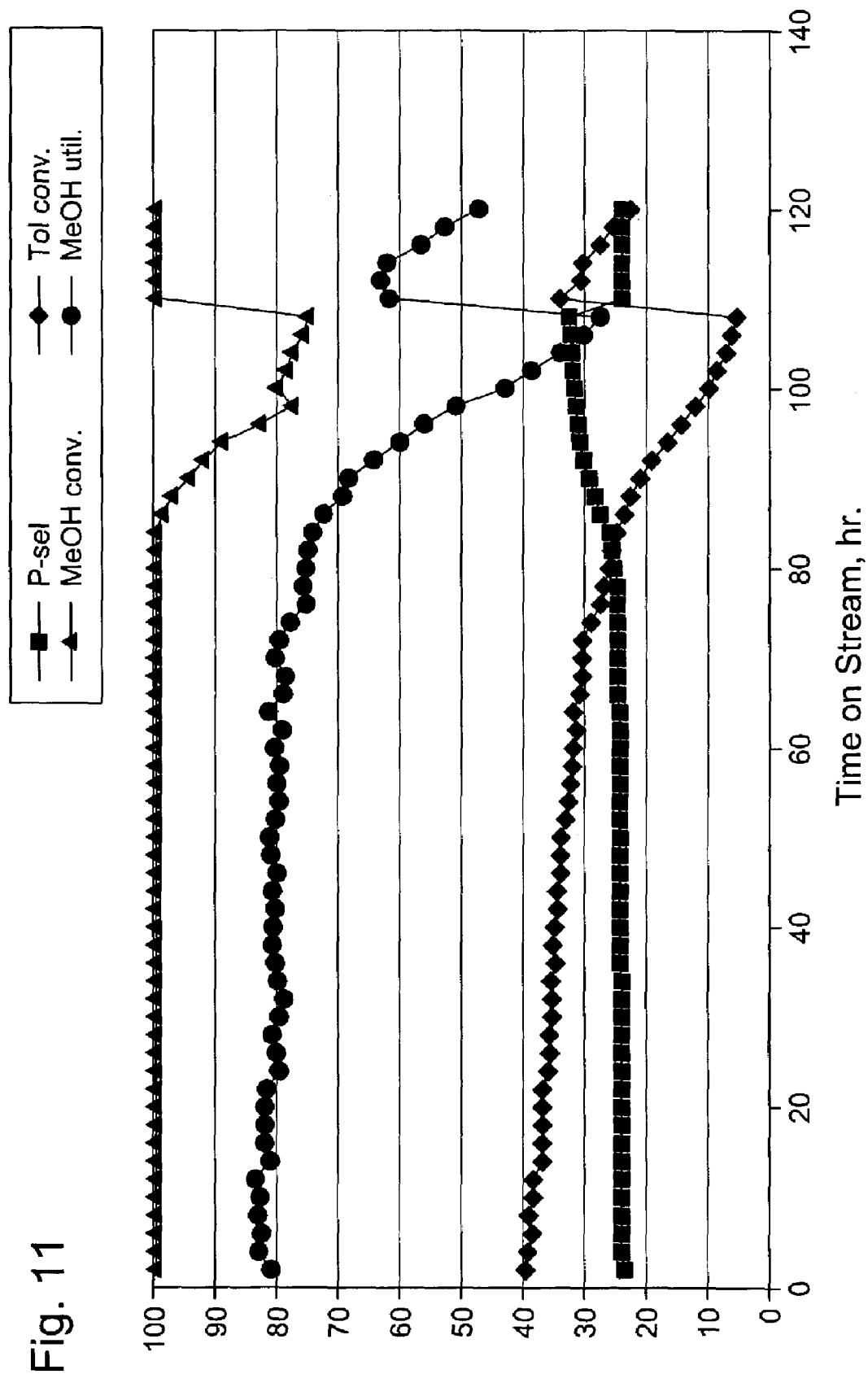
FIG. 11 is a graph depicting the test results of Example 6.

Toluene methylation was carried in a fixed-bed downflow reactor and over two grams of aluminosilicate catalyst composition of Example 5. The conditions for the test included a temperature of 500° C., a pressure of 15 psig, a $H_2$ to hydrocarbon molar ratio of 0.8, and a weight hour space velocity of 3.9 hr$^{-1}$ based on the catalyst for the first seventy-five hours of the test and thereafter a weight hour space velocity of 5.07 hr$^{-1}$ based on the catalyst, and a methanol to toluene mole ratio of 1:3. After running the test for about 110 hours, the catalyst was regenerated. The regeneration was carried out by first heating the catalyst under air flow of 50 cc/min. from room temperature to 530° C. and at a rate 3° C./min. The catalyst was maintained at 500° C. for 10 hours and then cooled to room temperature. For a 1:3 molar feed mixture, the maximum toluene conversion expected from reaction with methanol would be about 33%. The results of the tests are shown in FIG. 11.

We claim:

1. A process for aromatics conversion comprising contacting, under conversion conditions, a feedstock suitable for aromatics conversion with a catalyst comprising a synthetic porous crystalline material having a 3-dimensional channel system comprising a first set of generally parallel channels each of which is defined by a 10-membered ring of tetrahedrally coordinated atoms, a second set of generally parallel channels which are also defined by 10-membered rings of tetrahedrally coordinated atoms and which intersect with the channels of the first set, and a third set of generally parallel channels which intersect with the channels of said first and second sets and each of which is defined by a 9-membered ring of tetrahedrally coordinated atoms.

2. The process recited in claim 1, wherein said synthetic porous crystalline material comprises a framework of tetrahedral atoms bridged by oxygen atoms, the tetrahedral atom framework being defined by a unit cell with atomic coordinates in nanometers shown in Table 1, wherein each coordinate position may vary within ±0.05 nanometer.

3. The process recited in claim 1, wherein the synthetic porous crystalline material has an X-ray diffraction pattern including d-spacing and relative intensity values substantially as set forth in Table 2.

4. The process recited in claim 1, wherein the synthetic porous crystalline material has a composition comprising the molar relationship $$X_2O_3:(n)YO_2$$

wherein n is at least about 5, X is a trivalent element, and Y is a tetravalent element.

5. The process recited in claim 4, wherein X is a trivalent element selected from the group consisting of boron, iron, indium, gallium, aluminum, and a combination thereof; and Y is a tetravalent element selected from the group consisting of silicon, tin, titanium, germanium, and a combination thereof.

6. The process recited in claim 5, wherein X comprises boron or aluminum and Y comprises silicon.

7. The process recited in claim 6, wherein X is aluminum.

8. The process recited in claim 7, wherein the silica to alumina molar ratio of said synthetic porous crystalline material is less than 1000.

9. The process recited in claim 1, wherein said catalyst further comprises at least one hydrogenation/dehydrogenationation metal.

10. The process recited in claim 9, wherein said at least one hydrogenation/dehydrogenation metal is selected from the group consisting of a Group VIII metal and a Group VIIB metal.

11. The process recited in claim 1, wherein said aromatics conversion is carried at conditions comprising a temperature of from about 200° C. to about 760° C., a pressure of from about atmospheric to about 200 atmospheres, and a weight hourly spare velocity of from about 0.08 hr$^{-1}$ to about 2000 hr$^{-1}$.

12. The process recited in claim 11, wherein said aromatics conversion comprises converting feedstock comprising aromatic compounds to a product comprising aromatic compounds which differ from said feedstock.

13. The process recited in claim 12, wherein said feedstock comprises at least one aromatic compound selected from the group consisting of:

(A) monocyclic alkylaromatic compounds represented by the formula:

I wherein:

R, R$^1$, and R$^2$ are independently selected from the group consisting of hydrogen and an alkyl or alkenyl group having 1 to about 12 carbon atoms; and, (B) bicyclic alkylaromatic compounds represented by the formula:

II wherein:

R$^3$ and R$^4$ are independently selected from the group consisting of hydrogen and an alkyl or alkenyl group having 1 to about 4 carbon atoms;

Y is an integer of from 0 to 2; and

Z is an integer of from 0 to 2.

14. The process recited in claim 13, wherein R, R$^1$, R$^2$, R$^3$, and R$^4$ are independently selected from the group consisting of hydrogen, methyl, ethyl, n-propyl, isopropyl, and n-butyl.

15. The process recited in claim 14, wherein said feedstock comprises at least one aromatic compound of formula I and R, R$^1$, R$^2$, R$^3$, and R$^4$ are independently selected from the group consisting of hydrogen, methyl and ethyl.

16. The process recited in claim 15, wherein said feedstock comprises at least one aromatic compound selected from the group consisting of benzene, toluene ethylbenzene, styrene, xylenes, 1,4-diethylbenzene, 1,2-diethylbenzene, 1,3,5-trimethylbenzene, 1,2,3-trimethylbenzene, 1,2,4-trimethylbenzene, 1,3,5-triethylbenzene, methylpropylbenzenes, ethylpropylbenzenes, dipropylbenzenes, diisopropylbenzenes, and triisopropylbenzenes.

17. The process recited in claim 15, wherein said feedstock comprises at least one aromatic compound selected from the group consisting of 1-methylnaphthalene, 2-methylnaphthalene, 1,2-dimethylnaphthalene, 1,2-diethylnaphthalene 2,3-dimethylnaphthalene, 2,3-dipropylnaphthalene 2,6-dimethylnaphthalene, and 2,6-dibutyl-naphthalene.

18. The process recited in claim 12, wherein said at least one aromatic compound present in said feedstock is selected from the group consisting of benzene, toluene, xylenes, and mixtures thereof.

19. The process recited in claim 12, wherein said aromatics conversion is selected from the group consisting of the isomerization of dialkyl substituted benzenes, the disproportionation of monoalkyl substituted benzenes, the alkylation of aromatic compounds, the transalkylation of aromatic compounds in the presence of polyalkylaromatic compounds, the dealkylation of alkylaromatic compounds, the isomerization of ethylbenzene to form xylenes, and the isomerization of dialkylnaphthalenes.

20. The process recited in claim 19, wherein said aromatics conversion is selected from the group consisting of toluene disproportionation, xylenes isomerization, and aromatics alkylation.

21. The process recited in claim 20, wherein the product comprises xylenes.

22. The process recited in claim 11, wherein said catalyst comprising ITQ-13 further comprises a selectivating agent.

23. The process of claim 22, wherein said selectivating agent is selected from the group consisting of silica, coke, phosphorus, alkaline earth metal oxide, rare earth metal oxides, lanthanum oxide, boron oxide, titania, antimony oxide, manganese oxide, titania and mixtures thereof.

24. The process recited in claim 12, wherein said aromatics conversion is aromatics alkylation or toluene disproportionation.

25. The process recited in claim 12, wherein said aromatics conversion is xylenes conversion/ethyl benzene conversion.

26. The process recited in claim 25, wherein said catalyst further comprises at least one hydrogenation/dehydrogenationation metal.

27. The process recited in claim 25, wherein said feedstock is a C$_8$ mixture containing ethylbenzene and xylenes in which the para-xylene is less than thermodynamic equilibrium and said xylenes conversion/ethyl benzene conversion is carried out by contacting said $C_8$ mixture with a catalyst suitable for ethylbenzene conversion to form a ethylbenzene depleted product and contacting said ethylbenzene depleted product with said catalyst comprising ITQ-13.

28. The process recited in claim 12, wherein said aromatics conversion is the formation of xylenes by the methylation of toluene.

29. The process recited in claim 28, where said methylating agent is methanol and at least 60 percent of said methanol is converted.

30. The process recited in claim 11, wherein said aromatics conversion comprises converting non-aromatic compounds to aromatic compounds.

31. The process recited in claim 30, wherein said aromatics conversion is selected from the group consisting of the conversion of light paraffins to aromatics and olefins, the conversion of light olefins to aromatics, the conversion of naphtha to aromatics, the dehydrogenation of cycloaliphatics having 6 member rings, the conversion of oxygenates to aromatics.

32. The process recited in claim 31, wherein said catalyst further comprises at least one hydrogenation/dehydrogenationation metal.

33. The process recited in claim 32, wherein said at least one hydrogenation/dehydrogenationation metal is a Group VIII metal.

34. The process recited in claim 30, wherein the product of the aromatics conversion is selected from the group consisting of benzene, toluene, xylenes, and mixtures thereof.

* * * * *